United States Patent [19]

Henry

[11] 4,415,926
[45] Nov. 15, 1983

[54] INSPECTION OF ELONGATED MATERIAL

[75] Inventor: James W. Henry, Kingsport, Tenn.

[73] Assignee: Eastman Kodak Company, Rochester, N.Y.

[21] Appl. No.: 382,990

[22] Filed: May 28, 1982

[51] Int. Cl.³ .............................................. H04N 7/18
[52] U.S. Cl. .................................... 358/107; 250/563; 356/238; 377/16; 377/53
[58] Field of Search .......................... 358/107, 106, 93; 250/563; 377/3, 16, 24, 53; 356/238

[56] References Cited

U.S. PATENT DOCUMENTS

| | | | |
|---|---|---|---|
| 3,114,797 | 12/1963 | Williams | 358/105 |
| 3,584,225 | 6/1971 | Lindemann | 250/562 |
| 3,700,903 | 10/1972 | Adler | 358/106 |
| 3,985,451 | 10/1976 | Plöckl | 356/238 |
| 4,057,350 | 11/1977 | Craig | 356/238 |
| 4,232,336 | 11/1980 | Henry | 358/107 |
| 4,240,110 | 12/1980 | Henry | 358/107 |

Primary Examiner—Howard Britton
Attorney, Agent, or Firm—John F. Stevens; Daniel B. Reece, III

[57] ABSTRACT

Disclosed is a method for characterizing crimped tow for subsequent identification or quality control comprising the steps of obtaining length measurements of the individual crimps in a sample of the tow, graphically representing the measurement distribution of a sufficient quantity of the tow until a pattern is established, and using the pattern as a standard against which other tow is compared.

4 Claims, 4 Drawing Figures

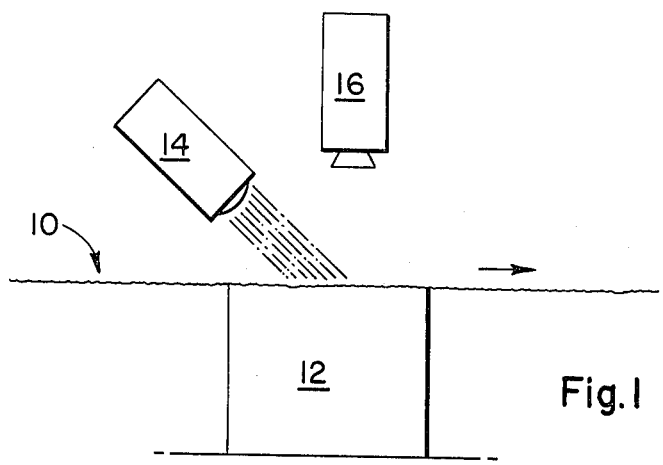
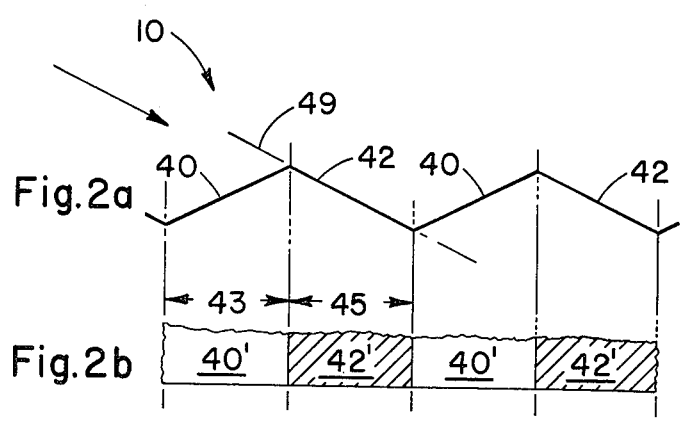

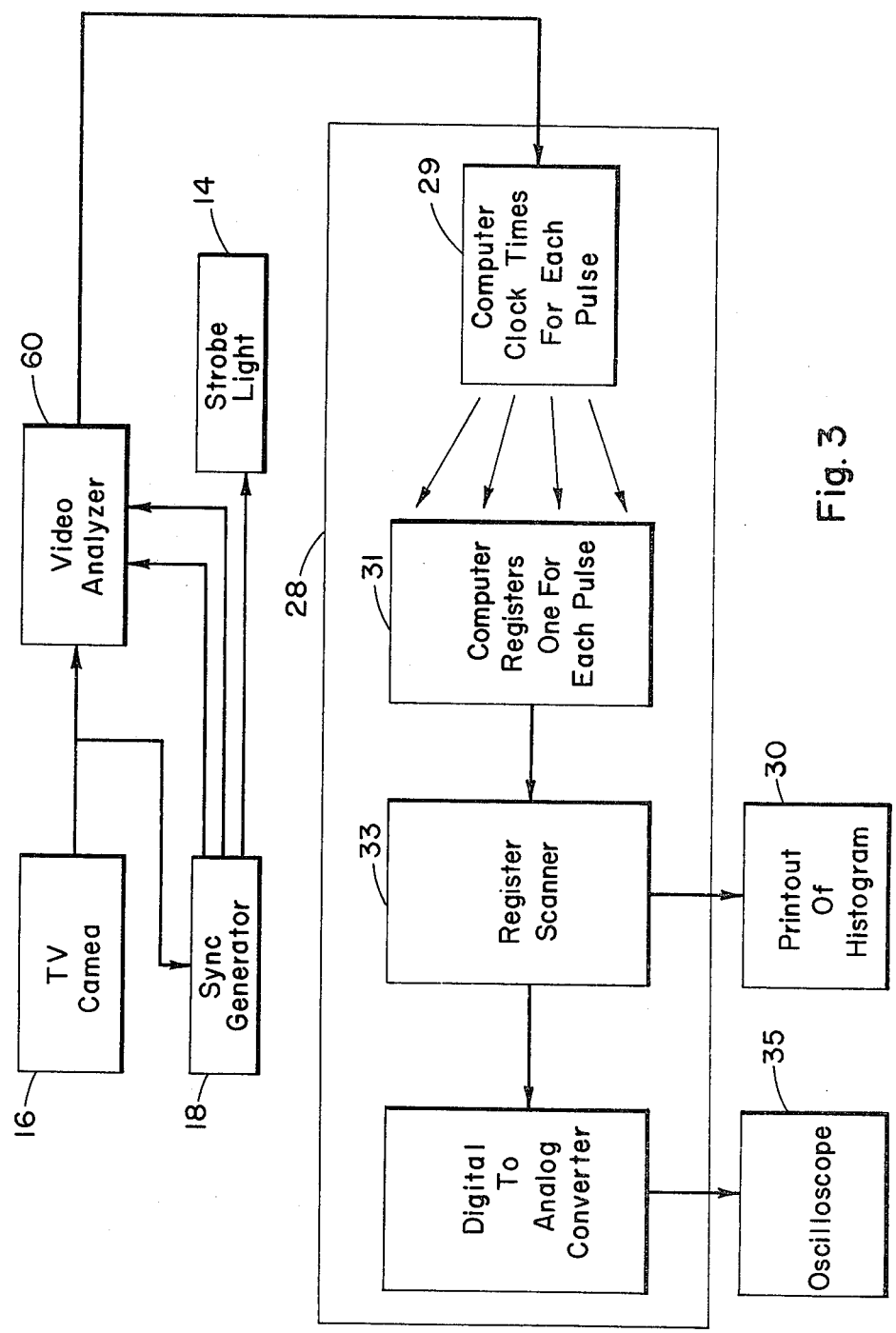

4,415,926

INSPECTION OF ELONGATED MATERIAL

DESCRIPTION

Technical Field

This invention relates generally to a method for inspecting and characterizing elongated material. More specifically, this invention relates to a method for inspecting elongated material such as strands, sheets, bundles or webs for the size distribution of irregularities within a given length. Data obtained from such inspection may be used for quality control and identification purposes.

This invention is particularly useful in monitoring production lines where continuous lengths of sheet or fibrous material is produced. Although various inspection uses will be apparent to those skilled in the art, the present invention will be described herein mainly in reference to the production of fiber tow which has been crimped. Such fiber tow, e.g., cellulose acetate filter tow, is mechanically crimped for various reasons known to those skilled in the art. The present invention provides a method whereby crimp may be continuously monitored, and if faulty conditions are detected, appropriate steps can be taken before substantial loss results.

BACKGROUND ART

Various electronic systems are presently known for detecting defects in continuous lengths of material. For example, U.S. Pat. No. 3,584,225 relates to a yarn inspection device which uses optical devices and electronic circuitry to detect defects in yarn. U.S. Pat. No. 3,114,797 relates to a television system for detecting differences or changes in shape, size, color, intensity or texture. Such differences or changes are detected by comparing a scene at one instant with an image produced from the same scene after a time delay. U.S. Pat. No. 3,700,903 relates to detection systems wherein a coherent light beam is used to scan the surface of an object in a repetitive pattern. An output signal is produced by light reflected from the object for determining characteristics of the surface of the object.

My U.S. Pat. Nos. 4,232,336 and 4,240,110, incorporated herein by reference, relate to the inspection of elongated material for surface irregularities for determining certain characteristics such as count.

DISCLOSURE OF INVENTION

The present invention provides a method for characterizing crimped tow for subsequent identification or quality control comprising the steps of obtaining length measurements of the individual crimps in a sample of the tow, graphically representing the measurement distribution of a sufficient quantity of the two until a pattern is established, and using the pattern as a standard against which other tow is compared.

Preferably, this is accomplished by (1) moving the material along a predetermined path,
(2) positioning a stroboscopic light source adjacent the path of the material so as to direct its light at an angle relative to the material such that surface variations thereof will make a pattern of light and shadowed areas,
(3) positioning a television camera adjacent the path of the material such that the illuminated portion of the material will be in its field of view,
(4) generating an electrical pulse at selected intervals to activate the light source for a predetermined length of time and to trigger the scanning of a frame by the television camera,
(5) converting the image of the frame developed by the television camera into a video signal, and
(6) analyzing the video signal to obtain information relating to crimp size, and
(7) feeding the information into a digital computer for further processing.

Such method provides a convenient and reliable means for monitoring production lines to obtain physical data therefrom which can be electronically processed as a quality control measure.

BRIEF DESCRIPTION OF THE DRAWINGS

FIG. 1 is a partial schematic elevation view illustrating a preferred arrangement of elongated material, television camera, and stroboscope.

FIG. 2a is an elevation views of crimped fiber tow.

FIG. 2b is a plan view, shown diagrammatically, of fiber tow crimped and the direction of light beam from the stroboscope.

FIG. 3 is a diagram of the electrical components used in this invention.

BEST MODE FOR CARRYING OUT THE INVENTION

Referring to FIG. 1, irregular filamentary material, e.g., a continuous band of crimped fiber tow 10, is fed over support 12 in the direction indicated. For the sake of simplicity, the filamentary material will sometimes be referred to herein as tow. The tow generally moves at a rapid rate, for example, about 20 feet per second, but, of course, the speed may be much slower or much faster. Support 12 may be placed in a convenient position anywhere along the path of the crimped tow in various conventional operations well known in the art, or may be a separate inspection operation.

Stroboscope 14 is positioned adjacent the band of tow 10 so as to illuminate a portion of tow 10 as it passes over support 12. Stroboscope 14 is positioned at an angle relative to the direction of movement of tow 10 as shown on FIG. 1 to create a pattern of alternate light and dark strips on the tow as described hereinafter. Television camera 16 is placed in close proximity to stroboscope 14 in a manner such that the pattern of light and dark strips created by the light on the crimped tow will be in its field of view. Preferably, camera 16 is aimed substantially directly at a generally linear section of the tow. Also, the stroboscope 14 is directed towards the tow at an angle such that the generally parallel rays of light are substantially parallel to the tow sections at the maximum anticipated crimp angle.

FIG. 2b is a diagrammatic sketch illustrating in somewhat simplified form the section of tow shown in FIG. 2a. FIG. 2b illustrates the principals involved in creating light and dark strips on a section of tow by directing a beam of light at an angle to the crimp. Preferably the beam of light is collimated in at least one plane, i.e., the plane of the paper. Light from the direction illustrated by the arrow creates light strips 40 and dark strips or shadows 42 on the crimped tow 10. These alternating light strips 40 and dark strips 42 are detected by television camera 10 and appear in the video signal developed by camera 10. The term "crimp length" as used herein is intended to mean the distance between adjacent low points or high points on the crimped tow. For example, FIG. 2 illustrates two crimp lengths.

As shown in the diagram of FIG. 3, the television camera 16, the synchronization pulse of which is controlled by the pulse generator 18, feeds its video signal into a video analyzer system 60. The electrical signal from the video analyzer is fed to a computer 28, which is connected to print-out machine 30. Coordination of television camera 16 and stroboscope 14 is maintained by pulse generator 18.

The number of alternating light strips and shadow strips per unit length, and the relative width of such strips is therefore transformed into a video signal for analysis.

The video signal from the television camera is processed by a system shown diagrammatically in FIG. 3. The television camera 16 is synchronized as to frame rate and scanning rate by synchronization generator 18. The vertical synchronization pulse from the generator is used to trigger the stroboscopic light source so that at the beginning of each field scan a pulse of light is triggered to illuminate the tow band. The image reflected through the camera lens to the sensitive vidicon tube is stored in the tube and is read out by the scanning electron beam which generates the video signal. Because of the extremely short pulse of light, the image stored on the tube is not blurred due to movement of the tow. The video signal from the camera 16 is transferred to a video analyzer 60 where a selected group of luminance signals along a line perpendicular to the scanning lines of the picture are analyzed and presented as a slow scan video signal. The composite picture of the full television frame with an added graphic display of the slow scan video signal may be shown on a television monitor. The slow scan television signal is converted to pulse rate and wave length to pulse duty cycle.

The video signal produced by a standard television camera is an electrical signal characterized by a content of electrical alternating wave frequencies ranging from 30 hertz to as high as 35 magahertz. The amplitude of the waves contained within this band of frequencies defines the brightness of the portion of the television picture associated with the wave. The frequency defines the size of the picture element associated with the wave portion. High amplitudes represent bright picture elements. High frequencies represent small picture elements.

The operation of the video analyzer system 60, which is designed to convert the video signal received from a standard television camera into a waveform suitable for being introduced into a computer, may be described as follows.

Electrical analysis of quasi periodic signals produced by optical scanning of pseudo random patterns is carried out using a system generally designated as a tracking filter. Such a filter consists of a voltage controlled oscillator (in which the frequency of the oscillator is determined by the amplitude of the direct electrical voltage applied to its control terminals), a phase discriminating circuit (which compares the phase of the voltage controlled oscillator output to that of the signal to be tracked), a feedback loop (which applies the direct voltage output of the phase discriminator to the input voltage control terminal of the oscillator), and an amplifier to amplify the direct voltage output of the phase discriminator. The direct voltage output of the tracking filter is applied to a voltage quantizer. Such a quantizer produces a series of fixed amplitude voltage at terminals assigned to produce voltage when the amplitude of the input voltage to the system attains the level corresponding to that assigned for the given output terminal. By using such a device a voltage output is made available as the level of input voltage reaches each level of quantization. Varieties of these devices are commercially available which permit programming of the terminal outputs so that only the terminal corresponding to the voltage level input existing at a given time is energized and all other terminals are de-energized. This type of device is especially useful in the practice of this invention.

Using the output voltage produced by the voltage quantizer, it is possible to accurately establish a voltage level so that the energizing of a given terminal of the voltage quantizer always produces a voltage of exact amplitude. Since only one terminal is energized at a time, and that terminal corresponds to a given voltage input to the quantizer, it is possible to establish a time during which the given voltage input existed. This time period can be translated into electrical voltage or a digital signal by appropriate integration or digital timing systems.

The level of voltage applied to the quantizer input is directly related to the instantaneous frequency being tracked by the tracking filter. Thus, if the filter is tracking a voltage produced by scanning a random pattern, the voltage will represent the "frequency" or crimp length of the pattern at the point being scanned.

The quantizer output is used to control the time accumulation of a group of timers 29 assigned to each quantizer level terminal. Output from the terminal activates the timer, which times the duration of the signal. An integrator may be used as a timer, and the signal voltage output directed to a voltage quantizer. There are as many integrators used in the system as there are ordinates to be displayed in the graphic depiction of frequency distribution.

Each output terminal of a group of quantizers is fitted with a light emitting diode display. These lamps are arrayed in vertical columns with the light designating the lowest voltage level at the bottom and each successively higher voltage level placed higher in the stack. One quantizer display is assigned to each voltage level terminal and the timer for the initial voltage quantizer fed by the signal produced from the tracking filter. The geometric arrangement of the displays is such that illumination of the lamps form a crude curve showing the relative distribution of texture frequency content for the surface under analysis. The computer 28 contains a count register circuit 31 and a resistor scanner 33, the output of which feeds a histogram printout machine 30.

In a digital configuration of the display system the direct voltage output from the tracking filter is fed to an analog-to-digital converter were the analog signal is translated to a binary representation of voltage level. This binary signal is supplied to a computer programmed to time the duration period over which the signal exists. A timing channel is made available for each voltage level of interest. The accumulated time for each channel is then displayed by suitable means such as cathode ray tube 35 display or a printout on paper.

As an example, a Cohu Electronics Type 1110 video camera is arranged to photograph a band of fiber arrayed as a ribbon and textured in a pseudo random pattern of sharply folded accordian crimps. The video signal from this camera is recorded using a video recorder. The photographs are taken of the ribbon running through manufacturing machinery at a point immediately after the crimps are imparted and prior to packaging of the ribbon. The video recording is later played back into the input of a Colorado Video Type 310 video analyzer where a slow scan video signal is derived from the brightness level signal produced along a line vertically bisecting the video picture display. The slow scan video signal is induced into an Intersil Type 565 phase lock loop intergrated circuit which incorporates a voltage controlled oscillator, a phase discriminator network, and operational amplifiers which produce from the voltage feedback signal a DC signal directly proportional to the instantaneous oscillator running frequency. The DC signal produced by the phase lock loop integrated circuit is suitably filtered using a ladder type filter to remove the oscillator frequency thereby leaving a modulated dc signal proportional to the oscillator frequency. Suitable capacitors and resistors are connected to the phase lock loop circuit to set the normal running (center) frequency of the oscillator. This free running frequency is adjusted to be 2,400 Hz. The DC signal from the phase lock loop is amplified using an R.C.A. Type 3130 operational amplifier and directed to the input terminals of a National Type LM 3914 N linear display driver integrated circuit. This device serves as a voltage quantizer producing an output voltage of constant amplitude at each of ten terminals as the input voltage level rises or falls to exist within that level of amplitude. Each of the ten terminals of the National Type LM 3914 N circuit are directed to a single operational amplifier assigned to that terminal. Suitable adjustable biasing potentiometers are interfaced with the operational amplifier to permit adjustment of the amplifier bias so that appropriate voltages can be obtained from the amplifier output for each of the states which the quantizer terminals attain for voltage level present or not present.

The potentiometers are adjusted for each of the ten operational amplifiers to produce a terminal voltage of 4.2 volts when the input voltage to the device exists at a level within the range of voltage assigned to the terminal energized. A voltage of zero volts is set to exist when the terminal is not energized because of the input voltage of the device existing at a level other than the range assigned to the terminal. The output signals of each of the ten amplifiers are directed to a bootstrap integrator consisting of an RCA Type 3130 operational amplifier with a feedback capacitor of 0.5 microfarad with an input resistor of one megohm. Bias potentiometers are provided to null out normal drift voltage components. A potentiometer of 10K ohms is shunted from the output of the amplifier to a ground, and the tap of this potentiometer feeds the inverting input of the amplifier with voltage through a one megohm resistor. The outputs from each of the integrators are buffered and adjusted to match voltage levels using RCA Type 3130 operational amplifier which supply the input signal to each of ten National LM 3914 N linear display drivers. The terminals of each of these drivers supplies power to arrays of ten light emitting diodes. Each of these ten arrays were arrayed in ten vertical columns to provide a matrix of 100 light emitting diodes capable of displaying the histogram of frequency dispersion determined from the output of the phaselock loop tracking filter.

Video analyzer systems, as described generally above, are commercially available. For example, Video Analyzer 301 and Video Analyzer 302 are available from Colorado Video, Incorporated, of Boulder, Colo.

According to the present invention, the crimp length measurements are grouped for graphical representation, such as in a histogram where count (Y coordinate) would be plotted against crimp length (X coordinate). A suitable computer 28 well known to those skilled in the art contains a clock timer which measures the width of each pulse received, such width being representative of the length of each crimp. The computer registers one for each pulse width by circuit 31, and one bit is stored in the computer for each pulse at scanner 33. The computer may contain, for example, about 250 registers for storing bits.

One bit is entered into any one of the registers according to the size assignment given that register. For example, if a crimp length measuring 0.075 mm (0.0030") in wave-length is measured, one bit will be entered into the register assigned to this wavelength. As other crimp loops of differing measurements are encountered, one bit will be entered into the register assigned to represent that measured value. When any signal one of the register of the group of 250 is filled, compilation of the histogram is considered complete and the computer is directed to compute the relative percentage of the total bits accumuplated for each of the registers which have been partially or fully filled and a graphic plot of the contents of the registers consisting of the registers arrayed in a vertical column which each column parallel to its neighbors is generated. As soon as one register is full, the histogram is full and a new one is begun. A sufficient number of these histograms are made until a definite, recongnizable pattern is determined to exist. This pattern is like a "fingerprint" and may be considered as being representative of tow made under a particular set of conditions, i.e., a particular machine, machine adjustments, tow material and properties of the material. Tow subsequently tested by making histograms for patterns as described above, may be compared with the pattern previously established for the particular tow processing line for determination of quality or identification. If the pattern deviates from that previously established, it is a signal that something is wrong and corrective steps should be taken.

The invention has been described in detail with particular reference to preferred embodiments thereof, but it will be understood that variations and modifications can be effected within the spirit and scope of the invention.

We claim:

1. Method of characterizing crimped tow for subsequent identification or quality control comprising the steps of
   (a) obtaining length measurements of the individual crimps in a sample of said tow,
   (b) graphically representing the measurement distribution of a sufficient quantity of said tow until a pattern is established,
   (c) using the pattern established in step (b) as a standard against which other tow is compared.

2. Method according to claim 1 wherein the graphical representation is in the form of a histogram.

3. Method according to claim 1 wherein the length measurements are obtained by analyzing the video signal from a video camera's photograph of the crimped tow.

4. Method of characterizing crimped tow for subsequent identification or quality control comprising the steps of
   (a) illuminating a sample of crimped tow at an angle to reveal the individual crimps in said tow, (b) photographing at least a part of said sample with a video camera to form a video signal representing the photographed tow,
(c) analyzing said video signal to determine the luminance of picture elements,
(d) producing an electrical signal from said video signal, the waveform of said electrical signal conforming to the shape of the tow being analyzed,
(e) determining the slope transition intercepts of the waveform produced in (d) and using said intercepts to define the distance along the tow between selected intercepts,
(f) producing a graphic representation of the population of crimp convolutions with respect to their length determined in (e), and
(g) comparing the graphic representation so produced with respect to the graphic patterns produced by analysis of other crimped tow.

* * * * *